US00PP25190P3

(12) United States Plant Patent
Malone

(10) Patent No.: US PP25,190 P3
(45) Date of Patent: Dec. 30, 2014

(54) PLUM TREE NAMED 'LRP40A'

(50) Latin Name: *Prunus salicina*
Varietal Denomination: LRP40A

(75) Inventor: Michael T. Malone, Havelock North (NZ)

(73) Assignee: The New Zealand Institute for Plant and Food Research Limited, Auckland ( * ) Notice: Subject to any disclaimer, the term of this patent is extended or adjusted under 35 U.S.C. 154(b) by 287 days.

(21) Appl. No.: 13/506,924

(22) Filed: May 24, 2012

(65) Prior Publication Data

US 2013/0318663 P1 Nov. 28, 2013

(51) Int. Cl.
*A01H 5/00* (2006.01)

(52) U.S. Cl.
USPC ..... Plt./184

(58) Field of Classification Search
USPC ..... Plt./184
See application file for complete search history.

*Primary Examiner* — Kent L Bell
(74) *Attorney, Agent, or Firm* — Lathrop & Gage LLP

(57) ABSTRACT

A new and distinct plum variety is described. The variety results from a seedling of unknown parentage, the original plant was raised from seed and was planted at Havelock North, Hawke's Bay, New Zealand. In 2003, 'LRP40A' was identified as having potential as a new variety and was propagated for further trials. 'LRP40A' was selected for its desirable tree and fruit characteristics (firm red flesh, balanced fruit flavour), and the timing of the harvest.

3 Drawing Sheets

BACKGROUND TO THE INVENTION

Seedlings obtained from collecting seed from open pollinated fruit (Seed parent: unknown. Pollen parent: unknown.). The original plant was raised from seed and was planted out at Lawn Road, Havelock North, Hawke's Bay. New Zealand in 2000. In March 2003, the seedling coded 'LRP40A' was identified as having potential as a new variety due to its attributes of firm red flesh, balanced fruit flavour (a pleasant combination of sweetness, acidity and flavoursome fruit volatiles). Later in 2003, 'LRP40A' was first asexually propagated by budding onto 'Golden Queen' (not patented) peach seedling rootstock. 'Golden Queen' seedlings are a standard plum rootstock in New Zealand. The plant was first asexually reproduced in Napier, New Zealand. The trees were planted out in Hawke's Bay during the southern hemisphere winter of 2004. The resulting plants propagated true to type, demonstrating that the characteristics of the new variety are stable and transmitted without change through succeeding generations.

SUMMARY OF THE INVENTION

Under the New Zealand growing conditions 'LRP40A' is distinguished from varieties of common knowledge such as 'Royal Star' (U.S. Plant Pat. No. 7,192), 'Omega' (not patented) and its sibling 'LRP40/205' (U.S. Plant patent application Ser. No. 13/506,923) by the following characteristics:

The fruit of 'Royal Star' are cordate in shape whereas the fruit of 'LRP40A' is oblate in shape and typically ripens approximately two weeks later. The skin colour of 'Royal Star' fruit is darker than that of 'LRP40A' while the flesh colour is lighter.

The fruit of 'Omega' ripens significantly earlier than that of 'LRP40A', early February and late March to early April respectively.

The fruit of 'LRP40A' are larger, cordate in shape, moderately asymmetric with a lightly mottled skin colour while the fruit of 'LRP40A' is oblate in shape and slightly asymmetric with a darker more solid skin colour.

BRIEF DESCRIPTION OF FIGURES

The accompanying photographs show typical specimens of the, foliage, flowers and fruit of the new variety as depicted in colours as nearly true as is reasonably possible to make the same in a colour illustration of this character. The observations were made on mature trees which ranged in age between two and seven years old; 3-8 years from budding.

DETAILED DESCRIPTION OF THE VARIETY

Figure 1:
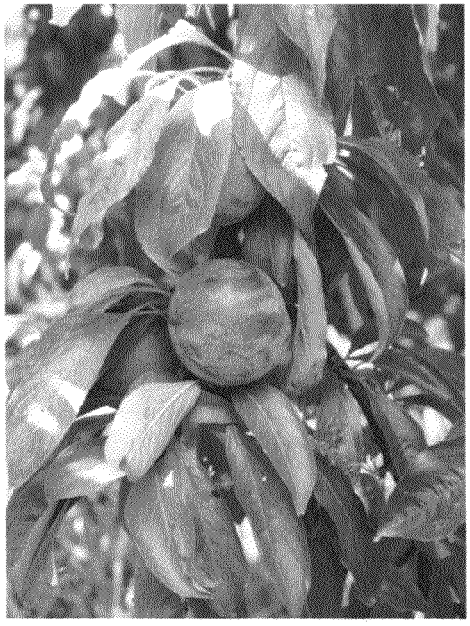
FIG. 1 shows fruit of 'LRP40A' on a two year old tree in the field (A and B).
Figure 1:
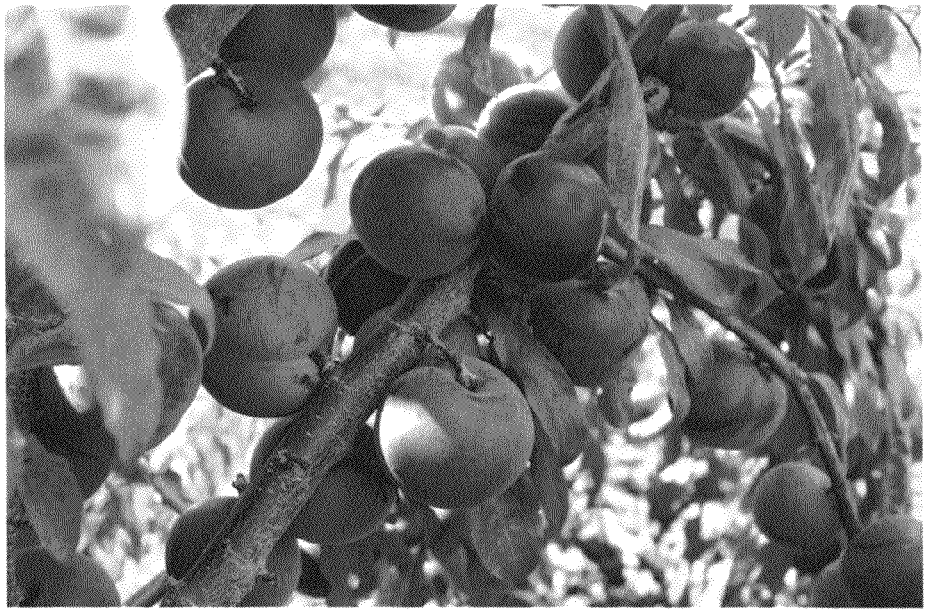
Figure 2:
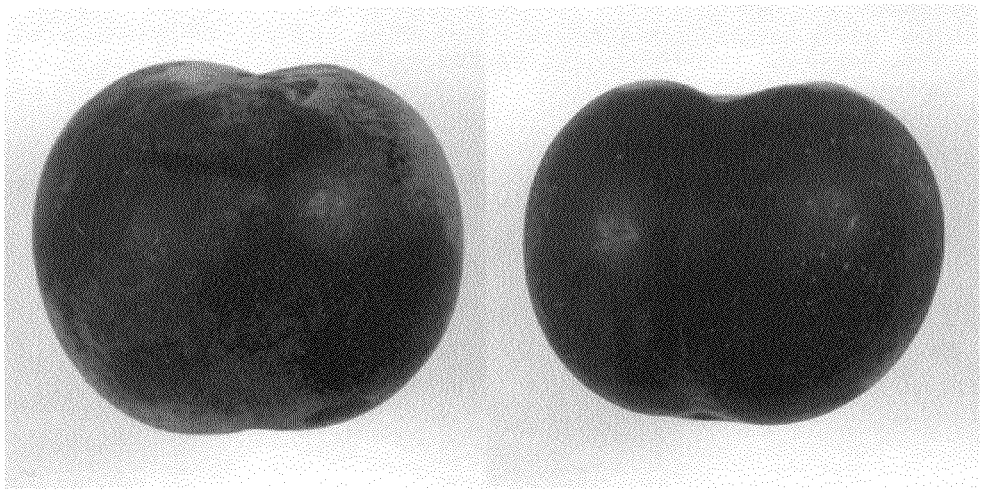
FIG. 2 shows fruit of 'LRP40A' (A) whole and (B) longitudinal section
Figure 2:
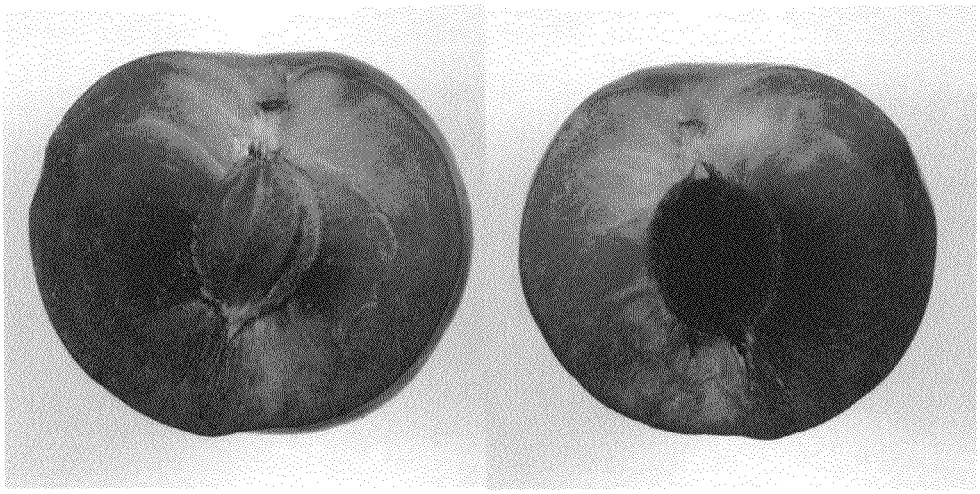
Figure 3:
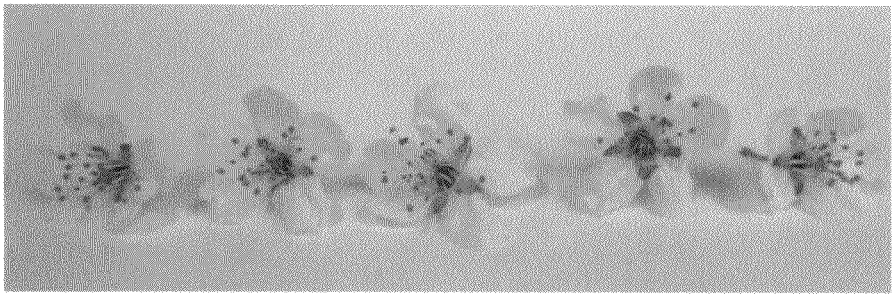
FIG. 3 shows 'LRP40A' (A) flowers at full bloom, (B) fully expanded leaf upper side, and (C) fully expanded leaf lower side.
Figure 3:
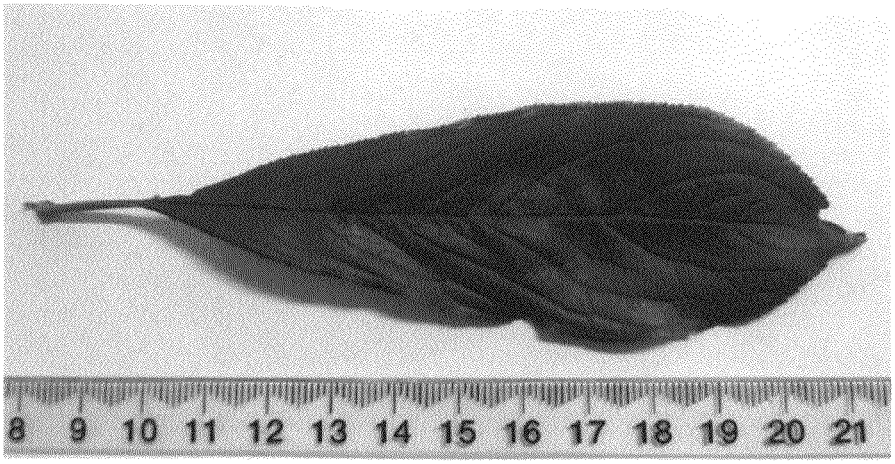
Figure 3:
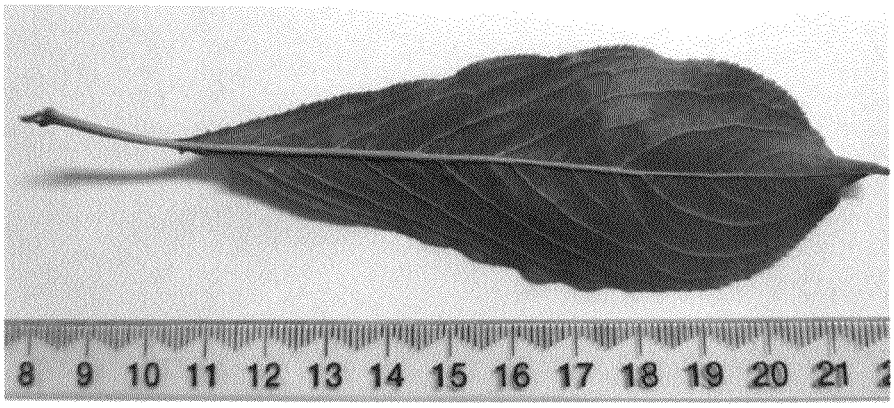

The following is a brief description of the new variety with colour terminology in accordance with The Royal Horticultural Society Colour Charts (R.H.S.C.C.) 2001 edition. The specimens described were grown in Hawke's Bay, New Zealand. The observations were made of the 2010-2012 seasons on mature trees which ranged in age between two and seven years old. Trees were grown under standard orchard practices.

Tree: Considered to be a small-medium sized tree, 'LRP40A' is observed to express similar vigour to plants of 'Satsuma' plum (not patented). The tree has a semi-upright branching habit similar to the variety 'Laroda' (not patented). The branches becoming more spreading with tree maturity. Mature tree height under managed conditions is within the range 5.0 m to 6.0 m, with a spread of 3.0 m to 4.0 m. 'LRP40A' scions are compatible with 'Golden Queen' peach seedlings which are the standard plum rootstock in New Zealand. Tree health is considered to be good under Hawke's Bay conditions in New Zealand with average yield of 50 kg per tree which is considered to be excellent under New Zealand conditions, with a similar precocity to commercially grown varieties in the area.

Trunk: Average circumference was measured to be approximately 215 mm, measured approximately 200 mm above the graft union. The trunk (observed on trees aged 3 years or older) was relatively smooth with a low amount of corky development, and coloured near grey-brown N199B and near brown 200B, branches were coloured near brown N200A with near greyed-orange 165A lenticles on both the trunk and branches. Branches (observed on trees aged 3 years or older) have a relatively smooth surface with a low amount of corky development. Main scaffold branch circumference (measured 10 cm from intersection with the trunk) ranged 6.7 cm to 11.3 cm. Weaker, divergent branches arise from the main scaffold limbs.

Shoots and buds: Fruit are borne on spurs and long shoots in a similar way to observed on trees of 'Shiro' (not patented). Fruit bearing spurs (observed on wood aged 3 years or older) average 12.2 mm in length. Vegetative shoots (observed in terminal positions within the tree canopy, post termination of annual growth) ranged 11.0 mm to 37.5 mm in length; the median length being 21.3 mm within the observed sample. The shoot surface texture is smooth, shiny, and near grey brown 199A in color. The vegetative buds (before opening) have an apex acute in shape, similar to those on the variety 'Eldorado' (not patented) and in a position slightly held out relative to the shoot, similar to those on the variety 'Satsuma'.

Leaves: The leaves examined were fully expanded and harvested from physiologically mature trees. The overall shape of the leaves was oblanceolate with a cuspidate tip, an acuminate base and serrulate margins. Leaves are clustered on spurs and singular on young branches. The colour of the upper side of the leaf was near green 137A and moderately glossy, while the lower side ranged near green 137C and 137D. The reticulate venation was coloured near yellow-green 145C extending to near green 145B on the underside at the end of the petiole. The average length of the blade was approximately 109.7 mm with an average width of approximately 38.6 mm. The nectaries are located predominately on the base of the leaf blade.

Petiole: The average petiole length of fully expanded leaves was 20.0 mm with an average width of 2.0 mm. The colour of the upper side was near yellow-green 144A. The colour of the underside is described above.

Flowers: Flower observations were made at full bloom which occurred mid to late September in Hawke's Bay, New Zealand. Flowers had a subtle fragrance. Flowers were clustered in groups of between one and three flowers.

Corolla: Five petals per flower, with an average length of 10.0 mm and average width of 8.0 mm. Petals are predominantly free with some touching or slightly overlapping. The petal shape was observed to be broadly obovate with smooth, slightly undulate margins. The petals were near white N155A on both the upper and lower petal surfaces.

Stamens: An average of 30 per flower. Filaments were an average length of 6.8 mm and translucent white in colour. The dorsifixed anthers were near yellow-orange 14A in colour. Pollen volume is moderate and grains are coloured near yellow-orange 14D.

Carpel: Pistil length was on average 8.5 mm in length. The stigma is positioned below the anthers.

Pedicel: Average length was 5.2 mm and width 1.1 mm. Coloured near yellow-green 144C.

Calyx: Five sepals per flower, average length of 3.0 mm and width 2.6 mm, medium ovate in shape, with an obtuse apex and smooth margin. Coloured on both upper and lower sepal surfaces near yellow-green 144B.

Fruit: Harvested late March early April in Hawke's Bay, New Zealand depending on the season. Fruit are borne on both spurs and long shoots.

Size: Fruit at harvest maturity were on average 118.54 g. Average height was 53.3 mm, width (lateral) 58.4 mm, and width (ventral) 63.1 mm.

Shape: Fruit were slightly asymmetric, and oblate in shape, with a depressed apex, shallow suture, truncate base, and a slightly depressed stem cavity. The depth of the stem cavity was 6.4 mm on average, with an average width of 23.4 mm.

Skin: Fruit surface is smooth with a medium bloom. Background colour near red 53A and 45D. The skin has medium tenacity and low tartness.

Over colour: Covers 95-99% of the fruit surface in a solid flush of colour ranging near greyed purple N187B to N187C with bloom, and near greyed purple 187A, near greyed purple N186C, and near purple N77A in the darkest areas with near red-purple 59A in lighter areas. Lenticels were abundant and coloured near yellow-orange 20B.

Flesh: Fine grained and consistently dense, with a medium firmness and a low expression of juice similar to fruit of the variety 'Laroda' (not patented). Colour is near greyed purple 185B and red-purple 60A in darkest areas and near red 45C in the lightest areas. The stone cavity colour is near greyed purple 187B and N77A.

Stone: Elliptic in shape in each of the lateral, ventral, and basal views, with an obtuse apex. The stone is observed to be symmetric or slightly asymmetric in the lateral view, with a fine grained texture similar to that observed in stones of the fruit from the variety 'Eldorado' (not patented). Average dry weight was 1.6 g, with an average height of 20.6 mm, width (lateral) 16.2 mm, and width (ventral) 11.3, with a narrow stalk end average width 2.5 mm. A clingstone type, the stone is semi-adherent to the flesh and has a colour near greyed orange 165 D.

Peduncle: Average length was 17.0 mm and width 3.0 mm. Coloured near greyed orange 166C.

Flavour: Flavour is sweet with low acidity. The flesh acidity level was medium, similar to that observed in fruit of the variety 'Shiro' (not patented) with medium sweetness similar to that observed in fruit of the variety 'Angeleno' (U.S. Plant Pat. No. 2,747). The soluble solids concentration (measured as ° Brix) averaged 17.2, ranging from a maximum of 18.7 to a minimum of 15.3.

Use: Fresh eating, potential for processing.

Keeping quality: Fruit stores for over 8 weeks at 0° C.

The invention claimed is:

1. A new and distinct plum tree substantially as illustrated and described.

* * * * *

A

B

A

B

A

B

C